United States Patent
Tomita Mitchell

(10) Patent No.: US 11,931,674 B2
(45) Date of Patent: *Mar. 19, 2024

(54) MATERIALS AND METHODS FOR PROCESSING BLOOD SAMPLES

(71) Applicant: Natera, Inc., San Carlos, CA (US)

(72) Inventor: Aoy Tomita Mitchell, Elm Grove, WI (US)

(73) Assignee: NATERA, INC., San Carlos, CA (US)

( * ) Notice: Subject to any disclaimer, the term of this patent is extended or adjusted under 35 U.S.C. 154(b) by 255 days.

This patent is subject to a terminal disclaimer.

(21) Appl. No.: 16/839,319

(22) Filed: Apr. 3, 2020

(65) Prior Publication Data

US 2020/0316498 A1    Oct. 8, 2020

Related U.S. Application Data

(60) Provisional application No. 62/829,320, filed on Apr. 4, 2019.

(51) Int. Cl.
*B01D 21/26* (2006.01)
*B01L 3/00* (2006.01)
*B04B 5/04* (2006.01)

(52) U.S. Cl.
CPC .......... *B01D 21/262* (2013.01); *B01L 3/5082* (2013.01); *B04B 5/0414* (2013.01)

(58) Field of Classification Search
CPC ..... B01D 21/262; B01D 21/26; B01L 3/5082; B01L 2200/16; B01L 3/50215; B01L 3/5021; B04B 5/0414; A01N 1/0215; A01N 1/0263; A61B 5/15003; A61B 5/150755; A61B 5/154

See application file for complete search history.

(56) References Cited

U.S. PATENT DOCUMENTS

| | | | | |
|---|---|---|---|---|
| 3,713,775 A | * | 1/1973 | Schmitz | B04B 5/0421 |
| | | | | 422/918 |
| 3,957,654 A | * | 5/1976 | Ayres | B01L 3/50215 |
| | | | | 422/918 |
| 5,180,812 A | | 1/1993 | Dower et al. | |
| 5,258,423 A | * | 11/1993 | Crabb | A61L 2/0035 |
| | | | | 523/136 |
| 5,319,071 A | | 6/1994 | Dower et al. | |
| 5,464,937 A | | 11/1995 | Sims et al. | |
| 5,488,032 A | | 1/1996 | Dower et al. | |
| 5,492,888 A | | 2/1996 | Dower et al. | |

(Continued)

FOREIGN PATENT DOCUMENTS

| | | |
|---|---|---|
| BR | 112017023232 A2 | 8/2018 |
| CA | 2875281 A1 | 12/2013 |

(Continued)

OTHER PUBLICATIONS

English Translation of Patent Document DE202014010872U1, Assignee: Dennemeyer & Associates, published Feb. 2017. (Year: 2017).*

(Continued)

*Primary Examiner* — Joseph W Drodge

(57) ABSTRACT

Provided herein are materials and methods relating to cell-free DNA. In particular, the technology relates to methods and materials for the preparation and handling of blood samples for future use in applications involving cell-free DNA.

10 Claims, 1 Drawing Sheet

(56) References Cited

U.S. PATENT DOCUMENTS

| | | | |
|---|---|---|---|
| 5,569,582 A | 10/1996 | Tavernarakis et al. | |
| 5,595,890 A | 1/1997 | Newton et al. | |
| 5,645,988 A | 7/1997 | Vande Woude et al. | |
| 5,736,033 A * | 4/1998 | Coleman | B01D 21/26 |
| | | | 210/222 |
| 6,475,175 B1 * | 11/2002 | Rivera | A61M 1/0209 |
| | | | 604/4.01 |
| 7,824,559 B2 * | 11/2010 | Dorian | A61P 17/02 |
| | | | 494/67 |
| 8,609,338 B2 | 12/2013 | Mitchell et al. | |
| 9,290,815 B2 | 3/2016 | Di Pasquale et al. | |
| 10,385,396 B2 * | 8/2019 | Mitchell | C12Q 1/6886 |
| 10,472,680 B2 * | 11/2019 | Mitchell | C12Q 1/6827 |
| 11,707,701 B2 * | 7/2023 | Tomita Mitchell | B01D 21/262 |
| | | | 210/787 |
| 2003/0148301 A1 | 8/2003 | Aono et al. | |
| 2003/0191005 A1 * | 10/2003 | Coelho | A61B 5/153 |
| | | | 494/43 |
| 2004/0115629 A1 | 6/2004 | Panzer et al. | |
| 2004/0136967 A1 | 7/2004 | Weiss et al. | |
| 2004/0151742 A1 * | 8/2004 | Beilfuss | A01N 37/02 |
| | | | 514/159 |
| 2006/0014179 A1 | 1/2006 | Roberts | |
| 2006/0068369 A1 * | 3/2006 | Coelho | A61M 1/0231 |
| | | | 435/284.1 |
| 2006/0088871 A1 | 4/2006 | Finkelstein et al. | |
| 2007/0134658 A1 | 6/2007 | Bohmer | |
| 2007/0207186 A1 * | 9/2007 | Scanlon | B29C 55/26 |
| | | | 623/1.42 |
| 2008/0020390 A1 | 1/2008 | Mitchell et al. | |
| 2008/0164204 A1 * | 7/2008 | Hatamian | B01L 3/5021 |
| | | | 210/516 |
| 2009/0087847 A1 | 4/2009 | Lo et al. | |
| 2009/0280479 A1 | 11/2009 | Hoon et al. | |
| 2010/0012598 A1 * | 1/2010 | DiCesare | B01L 3/50215 |
| | | | 210/520 |
| 2010/0099074 A1 * | 4/2010 | Nolan | A61B 5/150251 |
| | | | 435/307.1 |
| 2010/0155343 A1 * | 6/2010 | Battles | G01N 1/4077 |
| | | | 210/523 |
| 2010/0167271 A1 * | 7/2010 | Ryan | G01N 33/56972 |
| | | | 435/5 |
| 2010/0326218 A1 | 12/2010 | Boeckh et al. | |
| 2011/0110931 A1 | 5/2011 | Matsui | |
| 2011/0111410 A1 * | 5/2011 | Ryan | C12Q 1/6806 |
| | | | 435/325 |
| 2012/0010085 A1 | 1/2012 | Rava et al. | |
| 2012/0021442 A1 | 1/2012 | Buhimschi et al. | |
| 2012/0034685 A1 | 2/2012 | Sparks et al. | |
| 2012/0251411 A1 * | 10/2012 | Jeon | B01L 3/5021 |
| | | | 422/548 |
| 2012/0270212 A1 | 10/2012 | Rabinowitz et al. | |
| 2012/0295810 A1 | 11/2012 | Quake et al. | |
| 2013/0071844 A1 | 3/2013 | Makino et al. | |
| 2013/0143219 A1 | 6/2013 | Mitchell et al. | |
| 2013/0231252 A1 | 9/2013 | Mitchell et al. | |
| 2013/0323727 A1 | 12/2013 | Huang et al. | |
| 2013/0344066 A1 | 12/2013 | Faham et al. | |
| 2014/0045181 A1 | 2/2014 | Lo et al. | |
| 2014/0113795 A1 * | 4/2014 | Emerson | B01L 3/50215 |
| | | | 422/131 |
| 2014/0274740 A1 * | 9/2014 | Srinivasan | C12Q 1/6809 |
| | | | 435/287.2 |
| 2015/0056617 A1 | 2/2015 | Whitt et al. | |
| 2015/0086477 A1 | 3/2015 | Mitchell et al. | |
| 2015/0167077 A1 | 6/2015 | Fehr et al. | |
| 2015/0246103 A1 | 9/2015 | Hazout | |
| 2016/0053320 A1 | 2/2016 | Schuh et al. | |
| 2016/0115541 A1 | 4/2016 | Schutz et al. | |
| 2016/0186239 A1 | 6/2016 | Sinha | |
| 2017/0114411 A1 | 4/2017 | Mitchell et al. | |
| 2017/0137882 A1 | 5/2017 | Goossens et al. | |
| 2017/0145475 A1 * | 5/2017 | Hunsley | C12Q 1/6806 |
| 2017/0152561 A1 | 6/2017 | Hamamah et al. | |
| 2017/0206311 A1 | 7/2017 | Craig et al. | |
| 2017/0218458 A1 | 8/2017 | Fan et al. | |
| 2017/0283788 A1 | 10/2017 | Khoja et al. | |
| 2017/0298427 A1 | 10/2017 | Buis et al. | |
| 2018/0142296 A1 | 5/2018 | Mitchell et al. | |
| 2018/0288982 A1 | 10/2018 | Sinha | |
| 2018/0303870 A1 | 10/2018 | Golobish et al. | |
| 2018/0320239 A1 | 11/2018 | Babiarz et al. | |
| 2018/0371531 A1 | 12/2018 | Quake et al. | |
| 2019/0112661 A1 * | 4/2019 | Khan | C12Q 1/6883 |
| 2019/0153521 A1 | 5/2019 | Mitchell et al. | |
| 2019/0153525 A1 | 5/2019 | Mitchell et al. | |
| 2019/0211376 A1 | 7/2019 | Quake et al. | |
| 2019/0360033 A1 | 11/2019 | Stamm et al. | |
| 2019/0367972 A1 * | 12/2019 | Mitchell | C12Q 1/6883 |
| 2020/0032340 A1 * | 1/2020 | Mitchell | C12Q 1/6886 |
| 2020/0109449 A1 | 4/2020 | Stamm et al. | |
| 2020/0121718 A1 | 4/2020 | Novik et al. | |
| 2020/0141925 A1 | 5/2020 | Liaw et al. | |
| 2020/0165678 A1 | 5/2020 | Mitchell et al. | |
| 2020/0181681 A1 | 6/2020 | Mitchell et al. | |
| 2021/0032692 A1 | 2/2021 | Mitchell et al. | |
| 2021/0139969 A1 | 5/2021 | Mitchell et al. | |
| 2021/0139983 A1 | 5/2021 | Mitchell et al. | |
| 2021/0139988 A1 | 5/2021 | Mitchell et al. | |
| 2021/0269879 A1 | 9/2021 | Mitchell et al. | |
| 2021/0301320 A1 | 9/2021 | Mitchell et al. | |
| 2022/0145391 A1 | 5/2022 | Mitchell et al. | |
| 2022/0267849 A1 | 8/2022 | Mitchell et al. | |
| 2022/0340963 A1 | 10/2022 | North et al. | |
| 2022/0356522 A1 | 11/2022 | Mitchell et al. | |

FOREIGN PATENT DOCUMENTS

| | | | |
|---|---|---|---|
| CN | 102892901 A | 1/2013 | |
| CN | 107849604 A | 3/2018 | |
| CN | 109661476 A | 4/2019 | |
| DE | 202014010872 U1 * | 2/2017 | G01N 33/48 |
| EA | 201792389 A1 | 5/2018 | |
| EP | 1325963 A1 | 7/2003 | |
| EP | 1325963 B1 | 9/2006 | |
| EP | 2551356 A1 | 1/2013 | |
| JP | 2004121087 A | 4/2004 | |
| JP | 2013509883 A | 3/2013 | |
| JP | 2016502849 A | 2/2016 | |
| WO | WO9623067 A1 | 8/1996 | |
| WO | WO9937773 A1 | 7/1999 | |
| WO | 0134844 A1 | 5/2001 | |
| WO | WO2004078999 A1 | 9/2004 | |
| WO | 2006/128192 A2 | 11/2006 | |
| WO | WO2011015944 A2 | 2/2011 | |
| WO | WO2011057061 A1 | 5/2011 | |
| WO | WO2011094646 A1 | 8/2011 | |
| WO | 2011/118603 | 9/2011 | |
| WO | WO2011118603 A1 | 9/2011 | |
| WO | WO2012122374 A2 | 9/2012 | |
| WO | WO2013159035 A2 | 10/2013 | |
| WO | WO2014099919 A2 | 6/2014 | |
| WO | 2014/145232 A2 | 9/2014 | |
| WO | WO2014143989 A1 | 9/2014 | |
| WO | 2014/194113 A2 | 12/2014 | |
| WO | WO2014194113 A2 | 12/2014 | |
| WO | 2015035177 A1 | 3/2015 | |
| WO | WO2015035177 A1 | 3/2015 | |
| WO | WO2015069933 A1 | 5/2015 | |
| WO | 2015138997 A1 | 9/2015 | |
| WO | WO2015138997 A1 | 9/2015 | |
| WO | WO2015169947 A1 | 11/2015 | |
| WO | WO2015178978 A2 | 11/2015 | |
| WO | WO2016001411 A1 | 1/2016 | |
| WO | WO2016028316 A1 | 2/2016 | |
| WO | 2016/063122 A1 | 4/2016 | |
| WO | WO2016063122 A1 | 4/2016 | |
| WO | 2016/123698 A1 | 8/2016 | |
| WO | WO2016123698 A1 | 8/2016 | |
| WO | WO2016176662 A1 | 11/2016 | |
| WO | WO2016205511 A1 * | 12/2016 | A61M 1/02 |
| WO | WO2017011329 A1 | 1/2017 | |

(56) References Cited

FOREIGN PATENT DOCUMENTS

| WO | 2017-045654 A1 | 3/2017 | |
|---|---|---|---|
| WO | WO2017091865 A1 | 6/2017 | |
| WO | 2017/190106 A1 | 11/2017 | |
| WO | WO2017190106 A1 | 11/2017 | |
| WO | WO2018145005 A1 * | 2/2018 | ............... B01L 3/14 |
| WO | 2018/085603 A1 | 5/2018 | |
| WO | WO2018085597 A1 | 5/2018 | |
| WO | WO2018085603 A1 | 5/2018 | |
| WO | WO2018119422 A1 | 6/2018 | |
| WO | WO2018237078 A1 | 12/2018 | |
| WO | WO2018237081 A1 | 12/2018 | |
| WO | WO2019006561 A1 | 1/2019 | |
| WO | WO2019008408 A1 | 1/2019 | |
| WO | WO2019053243 A1 | 3/2019 | |
| WO | WO2019109053 A1 | 6/2019 | |
| WO | WO2019118926 A1 | 6/2019 | |
| WO | 2020/076957 A1 | 4/2020 | |
| WO | WO2020131955 A1 | 6/2020 | |
| WO | 2020/206269 A1 | 10/2020 | |
| WO | 2020/206292 A2 | 10/2020 | |
| WO | WO2020206290 A1 | 10/2020 | |
| WO | 2021/055968 A1 | 3/2021 | |
| WO | 2022/015676 A1 | 1/2022 | |

OTHER PUBLICATIONS

Wheatley, Preservation of Biological Specimens with Isobutyl Methacrylate Polymer, Published in Science, vol. 94, Jul. 11, 1941, pp. 49-50 (Year: 1941).*
No Author Listed, "Quantitative Detection of Circulating Donor-Specific DNA in Organ Transplant Recipients (DTRT-Multi-Center Study) (DTRT)", ClinicalTrials.gov Identifier: NCT02109575., Apr. 10, 2014, Last updated Mar. 26, 2021, 9 pages.
No Author Listed, "The Journal of Heart and Lung Transplantation", Apr. 2012., vol. 31, Issue 4, Supplement, pp. A1-A4, S1-S310. https://www.google.de/searchq=The+Journal+of+Heart+and+Lung+Transplantation+Volume+31,+Issue+4,+Supplement&sourceid=ie7&rls=com.microsoft:en-US:IE-Address&ie=&oe=#spf=1604593918239, Last Accessed: Oct. 13, 2015., A1-A4.
18820195.8, "Extended European Search Report", dated Jan. 27, 2021, 9 pages.
18821381.3, "Extended European Search Report", dated Feb. 15, 2021, 9 pages.
Adamek, Martina et al., "A fast and simple method for detecting and quantifying donor-derived cell-free DNA in sera of solid organ transplant recipients as a biomarker for graft function", Clinical Chemistry and Laboratory Medicine : Journal of the Forum of the European Societies of Clinical Chemistry, vol. 54, No. 7, doi:10.1515/CCLM-2015-0622, ISSN 1437-4331, (Jul. 1, 2016), pp. 1147-1155.
Agbor-Enoh, et al., "Applying rigor and reproducibility standards to assay donor-derived cell-free DNA as a non-invasive method for detection for acute rejection and graft injury after heart transplantation", J Heart Lung Transplant, 36(9):1004-1012. doi: 10.1016/j.healun.2017.05.026. Epub May 20, 2017., 17 pages.
Agbor-Enoh, et al., "Cell-Free DNA to Detect Heart Allograft Acute Rejection", Circulation, Mar. 23, 2021;143(12):doi: 10.1161/CIRCULATIONHA.120.04908. Epub Jan. 13, 2021, 1184-1197.
Agbor-Enoh, S. et al., "Donor-derived cell-free DNA predicts allograft failure and mortality after lung transplantation", EBioMedicine, vol. 40, 2019, 541-553.
Ahmed, et al., "Cell Free DNA and Procalcitonin as Early Markers of Complications in ICU Patients with Multiple Trauma and Major Surgery", Clin Lab, Dec. 1, 2016;62(12) ; doi: 10.7754/Clin.Lab.2016.160615., 2395-2404.
Alachkar, "Serum and urinary biomarkers in acute kidney transplant rejection", Nephrol Ther., Feb. 2012:8(1): doi: 10.1016/j.nephro.2011.07.409. Epub Oct. 21, 2011, 13-19.
Almeida, et al., "Evaluation of 16 SNPs allele-specific to quantify post hSCT chimerism by SYBR green-based qRT-PCR", J Clin Pathol., Mar. 2013;66(3):. doi: 10.1136/jclinpath-2012-201224. Epub Jan. 2, 2013., 238-242.
Andargie, et al., "Cell-free DNA maps Covid-19 tissue injury and risk of death and can cause tissue injury", JCI Insight, Apr. 8, 2021;6(7):e147610. doi: 10.1172/jci.insight.147610, 20 pages.
Arshad, et al., "Elevated Cell-Free Mitochondrial DNA in Filtered Plasma Is Associated With HIV Infection and Inflammation", J Acquir Immune Defic Syndr., May 1, 2018;78(1): doi: 10.1097/QAI.0000000000001650., 111-118.
Avriel, et al., "Admission Cell Free DNA Levels Predict 28-Day Mortality in Patients with Severe Sepsis in Intensive Care", PLoS One., Jun. 23, 2014;9(6):e100514. doi: 10.1371/journal.pone.0100514. eColleection 2014., 7 pages.
Ayyadevara, et al., "Discrimination of primer 3'-nucleotide mismatch by taq DNA polymerase during polymerase chain reaction", Anal Biochem. Aug. 15, 2000, 284(1), 1-18.
Bai, et al., "Detection and quantification of heteroplasmic mutant mitochondrial DNA real-time amplification refractory mutation system quantitative PCR analysis: a single-step approach", Clin Chem., Jun. 2004;50(6); Epub Apr. 8, 2004., 996-1001.
Bergallo, et al., "A Novel TaqMAMA assay for allelic discrimination of TLR9 rs352140 polymorphism", J Virol Methods, May 2017;243. doi: 10.1016/j.viromet.2017.01.015. Epub Jan. 28, 2017., 25-30.
Bergallo, et al., "Evaluation of IFN-γ polymorphism+874 T/A in patients with recurrent tonsillitis by PCR real time mismatch amplification mutation assay (MAMA real time PCR)", Cytokine., Feb. 2015; 71(2): Epub Dec. 2014., 278-282.
Bezieau, et al., "High incidence of N and K-Ras activating mutations in multiple myeloma and primary plasma cell leukemia at diagnosis", Hum Mutat., Sep. 2001;18(3):. doi: 10.1002/humu.1777, 212-224.
Bienkowski, et al., "Liquide biopsy for minimally invasive heart transplant monitoring: a pilot study", J Clin Pathol., Aug. 2020;73(8): doi: 10.1136/jclinpath-2019-205926. Epub Dec. 5, 2019, 507-510.
Board, et al., "Detection of PIK3CA mutations in circulating free DNA in patients with breast cancer", Breast Cancer Res Treat, Apr. 2010;120(2): doi:10.1007/s10549-010-0747-9. Epub Jan. 28, 2010, 461-467.
Board, et al., "Multiplexed assays for detection of mutations in PIK3CA", Clin Chem., Apr. 2008; 54(4), 757-760.
Braun, et al., "Limitation of Circulating cfDNA Under the Use of a Cytokine Elimination Adsorber (CytoSorb) in Cardiac Surgery", The Thoracic and Cardiovascular Surgeon, Jan. 2018; 66(S01): S1-S110, 1 page.
Bronkhorst, et al., "The emerging role of cell-free DNA as a molecular marker for cancer management", Biomol Detect Quantif, Mar. 18, 2019;17:100087. doi: 1.1016/j.bdq.2019.100087., 23 pages.
Burgstaller, et al., "Mitochondrial DNA heteroplasmy in ovine fetuses and sheep cloned by somatic cell nuclear transfer", BMC Dev Biol., Dec. 21, 2007;7:141, 10 pages.
Cabel, et al., "Circulating tumor DNA changes for early monitoring of anti-PD1 immunotherapy: a proof-of-concept study", Ann Oncol., Aug. 1, 2017;28(8); doi: 1.1093/annonc/mdx212., 1996-2001.
Cagliani, et al., "Deoxyribonuclease Reduces Tissue Injury and Improve Survival After Hemorrhagic Shock", J Surg Res., May 2020; 249: doi: 1.1016/j.jss.2019.11.036. Epub Jan. 8, 2020., 104-113.
Castells, et al., "K-ras muations in DNA extracted from the plasma of patients with pancreatic carcinoma: diagnostic utility and prognostic significance", J Clin Oncol., Feb. 1999;17(2): doi: 10.1200/JCO.1999.17.2.578., 578-584.
Castleberry, et al., "Quantification of Circulating Cell-Free DNA in Pediatric Heart Transplant Recipients", Journal of Heart and Lung Transplantation, Apr. 1, 2011; 30(4): ISSN: 1053-2498, DOI: 10.1016/j.healun.2011.01.415, S139.
Castleberry, C. D. et al., "Quantification of Circulating Cell—Free DNA in Pediatric Heart Transplant Recipients", Journal of Heart and Lung Transplantation, vol. 30, No. 4, Apr. 1, 2011, S139.

(56) References Cited

OTHER PUBLICATIONS

Chan, et al., "Bioinformatics analysis of circulating cell-free DNA sequencing data", Clin Biochem., Oct. 2015;48(15); doi: 10.1016/j.clinbiochem.2015.04.022. Epub May 9, 2015., 962-975.
Chen, et al., "Non-invasive prenatal diagnosis using fetal DNA in maternal plasma: a preliminary study fo identification of paternally-inherited alleles using single nucleotide polymorphisms", BMJ Open, Jul. 22, 2015;5(7):e007648. doi: 10.1136/bmjopen-2015-007648., 8 pages.
Chen, et al., "Non-invasive prenatal diagnosis using fetal DNA in maternal plasma: a preliminary study of identification of paternally-inherited alleles using single nucleotide polymorphisms", BMJ Open, 5(7), 2015, 1-8.
Cheng, et al., "Cell-Free DNA in Blood Reveals Significant Cell, Tissue and Organ Specific injury and Predict Covid-19 Severity", medRxiv., Jul. 29, 2020;2020.07.27.20163188. doi: 10.1101/2020.07.27.20163188., 16 pages.
Chiu, et al., "Effects of blood-processing protocols on fetal and total DNA quantification in maternal plasma", Clin Chem., Sep. 2001;47((9): Pubmed PMID: 11514393., 1607-1613.
Chiu, et al., "Noninvasive prenatal exclusion of congenital adrenal hyperplasia by maternal plasma analysis: a feasibility study", Clin Chem., May 2002;48(5), 778-780.
Chu, et al., "A novel approach toward the challenge of accurately quantifying fetal DNA in maternal plasma", Prenat Diagn., Dec. 2010;30(12-13): doi: 10.1002/pd.2656, 1226-1229.
Clementi, et al., "The Role of Cell-Free Plasma DNA in Critically Ill Patients with Sepsis"Blood Purif., 2016;41(1-3): doi: 10.1159/000440975. Epub Oct. 20, 2015, 34-40.
Crespo et al., Pre-transplant Donor-Specific T-cell Alloreactivity Is Strongly Associated With Early Acute Cellular Rejection in Kidney Transplant Recipients Not Receiving T-cell Depleting Induction Therapy. PLoS One. Feb. 17, 2015;10(2):e01 17618. doi: 10.1371/journal.pone.0117618. eCollection 2015.
Daly, "Circulating donor-derived cell-free DNA: a true biomarker for cardiac allograft rejection", Ann Transl Med., Mar. 2015;3(4):47. doi:10.3978/j.issn.2305-5839.2015.01.35, 6 pages.
Dandel, et al., "Non-invasive cardiac allograft rejection surveillance: reliability and clinical value for prevention of heart failure", Heart Fail Rev., Mar. 2021;26(2): doi: 10.1007/s10741-20-10023-3. Epub Sep. 5, 2020., 319-336.
Dastsooz, et al., "Multiplex ARMS PCR to Detect 8 common Mutations of ATP7B Gene in Patients With Wilson Disease", Hepat Mon., May 16, 2013;13(5):e8375. doi: 10.5812/hepatmon.8375. eCollection 2013., 7 pages.
De Vlaminck, et al., "Circulating cell-free DNA enables noninvasive diagnosis of heart transplant rejection", Sci Transl Med., Jun. 18, 2014;6(241):241ra77. doi: 10.1126/scitranslmed.3007803, 20 pages.
De Vlaminck, et al., "Circulating cell-free DNA enable noninvasive diagnosis of heart transplant refection", Sci Transl Med., Jun. 18, 2014;6(241):241ra77. Supplemental Materials., 6 pages.
De Vlaminck, et al., "Noninvasive monitoring of infection and rejection after lung transplantation", Proc Natl Acad Sci U S A.Oct. 27, 2015;112(43): doi: 10.1073/pnas.1517494112. Epub Oct. 12, 2015., 13336-13341.
Delgado, et al., "Characterization of cell-free circulating DNA in plasma in patients with prostate cancer", Tumoour Biol., Apr. 2013;34(2): doi: 10.1007/s13277-012-0634-6. Epub Dec. 27, 2012, 983-986.
Delgado, P. O. et al., "Characterization of cell-free circulating DNA in plasma in patients with prostate cance", Tumor Biol., vol. 34, 983-986, 2013.
Deshpande, et al., "Relationship Between Donor Fraction Cell-Free DNA and Treatment for Rejection in Heart Transplantation", Pediatric Transplantation, Jun. 2022; 26(4):e14264. https://doi.org/10.1111/petr.14264, 11 pages.
Dey, et al., "A plasma telomeric cell-free DNA level in unaffected women with BRCA1 or/and BRCA2 mutations: a pilot study. Oncotarget", Oncotarget, Dec. 29, 2017;9(3): doi: 10.18632/oncotarget.23767. eCollection Jan. 9, 2018., 4214-4222.

Ding, et al., "New Progress in Plasma Cell-free DNA in Clinical Applications", Progress in Modern Biomedicine, 2016; 18: 3476, 3593-3596.
Dwivedi, et al., "Prognostic utility and characterization of cell-free DNA in patients with severe sepsis", Crit Care, Aug. 13, 2012;16(4):R151.doi: 10.1186/cc11466., 11 pages.
Fleischhhacker, et al., "Circulating nucleic acids (CNAs) and cancer—a survey", Biochim Biophys Acta,Jan. 2007;1775(1): doi: 10.1016/j.bbcan.2006.10.001. Epub Oct. 7, 2006., 181-232.
García Moreira, et al., "Cell-free DNA as a noninvasive acute rejection marker in renal transplantation", Clin Chem., Nov. 2009;55(11): doi:10.1373/clinchem.2009.129072. Epub Sep. 3, 2009, 1958-1966.
Garnacho-Montero, et al., "Prognostic and diagnostic value of eosinopnia, C-reactive protein, procalcitonin, and circulating cell-free DNA in critically ill patients admitted with suspicion of sepsis", Crit care, Jun. 5, 2014;18(3):R116.doi: 10.1186/cc13908, 9 pages.
Ghanta, et al., "Non-invasive prenatal detection of trisomy 21 using tandem single nucleotide polymorphisms", PLoS One, Oct. 8, 2010;5(10):e13184. doi: 10.1371/journal.pone.0013184, 10 pages.
Gielis, et al., "Cell-Free DNA: An Upcoming Biomarker in Transplantation", Am J Transplant, Oct. 2015;15(10): doi: 10.1111/ajt.13387. Epub Jul. 16, 2015, 2541-2551.
Gielis, et al., "Plasma donor-derived cell-free DNA kinetics after kidney transplantation using a single tube multiplex PCR assay", PLoS One, 2018; 13(12): e0208207, 16 pages.
Geilis, E. M. et al., "Cell-Free DNA: An Upcoming Biomarker in Transplantation", American Journal of Transplantation, vol. 15, 2015, 2541-2551.
Glaab, et al., "A novel assay for allelic discrimination that combines the fluorogenic 5' nuclease polymerase chain reaction (TaqMan) and mismatch amplification mutation assay", Mutat Res., Nov. 29, 1999;430(1), 1-12.
Glaab, W. W. et al., "A novel assay for allelic discrimination that combines the fluorogenic 5' nuclease polymerase chain reaction (TaqMan) and mismatch amplification mutation assay", Mutation Research, vol. 430, 1999, 12 pgs.
Goncalves-Primo, A. et al., "Investigation of Apoptosis-Related Gene Expresseion Levels in Preimplantation Biopsies as Predictors of Delayed Kidney Graft Function", Transplantation, vol. 97, No.12, Jun. 27, 2014.
Gordon, et al., "An Algorithm Measuring Donor Cell-Free DNA in Plasma of Cellular and Solid Organ Transplant Recipients That Does Not Require Donor of Recipient Genotyping", Front Cardiovasc Med., Sep. 22, 2016;3:33. eCollection 2016., 10 pages.
Gordon, Paul et al., "An Algorithm Measuring Donor Cell-Free DNA in Plasma of Cellular and Solid Organ Transplant Recipients That Does Not Requre Donor of Recipient Genotyping", Frontiers in Cardiovascular Medicine, 2016, vol. 3.
Gormally, et al., "Amount of DNA in plasma and cancer risk: a prospective study", Int J Cancer, Sep. 20, 2004;111(5): doi: 10.1002/ijc.20327, 746-749.
Gotoh, et al., "Prediction of MYCN amplification in neuroblastoma using serum DNA and real-time quantitative polymerase chain reaction", J Clin Oncol., Aug. 1, 2005;23(22): PubMed PMID: 16051962., 5205-5210.
Gripp, et al., "*Homo sapiens* KRAS proto-oncogen, GTPase (KRAS), RefSeqGene (LEG_344) on chromosome 12". GenBank Submission; Accession No. NG_007524, version NG_007524.2, Aug. 16, 2020., 16 Pages.
Grskovic, et al., "Validation of a Clinical-Grade Assay to Measure Donor-Derived Cell-Free DNA in Solid Organ Transplant Receipients", J Mol. Diagn., Nov. 2016;18(6): doi 10.1016/j.jmoldx.2016.07.003. Epub 2016, 890-902.
Guedj, et al., "A refined molecular taxonomy of breast cancer", Oncogene, Mar. 1, 2012;31(9):1196-206. doi: 10.1038/onc.2011.301. Epub Jul. 25, 2011., 34 pages.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.
Hasi, et al., "Acetaldehyde dehydrogenase 2 SNP rs671 and susceptibility to essential hypertension in Mongolians: a case control study", Genet Mol Res., Mar. 29, 2011;10(1). doi: 10.4238/vol10-1gmr1056., 537-543.

(56) References Cited

OTHER PUBLICATIONS

Hidestrand, et al., "Highly sensitive noninvasive cardiac transplant rejection monitoring using targeted quantification of donor-specific cell-free deoxyribonucleic acid", J Am Coll Cardiol., Apr. 1, 2014;63(12). doi:10.1016/j.jacc.2013.09.029. Epub Oct. 16, 2013., 1224-1226.

Hidestrand, et al., "Highly Sensitive Transplant Rejection Surveillance Using Targeted Detection of Donor Specific Cell Free DNA", J Heart Lung Transplant, Apr. 2012; 31(4), S91-S92.

Hidestrand, et al., "Influence of temperature during transportation on cellfree DNA analysis", Fetal Diagn Ther., 2012; 31, 122-128.

Hidestrand, et al., "Quantification of Circulating Donor Specific Cell Free DNA Is an Exquisitely Sensitve Non-Invasive Indicator of Injury to the Donor Heart", J Heart Lung Transplant, 2013; 32, S101-S102.

Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.

Hoerning, et al., "Quantitative real-time ARMS-qPCR for mitochondrial DNA enables accurate detection of microchimerism in renal transplant recipients", Pediatr Transplant, Dec. 2011;15(8). doi:10.1111/j.1399-3046.2011.01581.x. Epub Oct. 4, 2011, 809-818.

Hou, et al., "Application of tetra primer ARMS-PCR approach for detection of Fusarium graminearm genotypes with resistance to carbendazim", Australian Plant Pathology, Jan. 1, 2013; 42(1), 73-78.

Huang, et al., "Circulating cell-free DNA levels correlate with postresuscitation survival rates in out-of-hospital cardiac arrest patients", Resuscitation, Feb. 2012;83(2): doi: 10.1016/j.resuscitation.2011.07.039. Epub Aug. 22, 2011., 213-218.

Huang, et al., "*Homo sapiens* TSC complex subunit 1 (TSC1), RefSeqGene (LRG-486) on chromosome 9", GenBank Submission; Accession No. NG_012386, version NG_012386.1, Sep. 21, 2020, 20 Pages.

Hudecova, "Digital PCR analysis of circulating nucleic acids", Clin Biochem., Oct. 2015;48(15): doi: 1.1016/j.clinbiochem.2015.03.015. Epub Mar. 28, 2015, 948-956.

Hugon, et al., "Influence of intention to adhere, beliefs and satisfaction about medicines on adherence in solid organ transplant recipients", Transplantation., Jul. 27, 2014;98(2): doi: 10.1097/TP.0000000000000221, 222-228.

Illumina, "HumanOmni1-Quad BeadChip", Illumina DNA Analysis, Pub. No. 370-21009-007, 2009, 1 page.

Illumina, "HumanOmni2.5-8 BeadChips: Next-Generation GWAS Content for Genotyping and CNV Analysis", Data Sheet: DNA Analysis, Pub. No. 370-2011-008, 2011, 1 page.

Jing, et al., "Cell-free DNA: characteristics, detection and its applications in myocardial infarction", Curr Pharm Des., 2013;19(28): doi: 10.2174/13816128113192801012., 5135-5145.

Jordan, et al., "Donor-derived Cell-free DNA Identifies Antibody-mediated Rejection in Donor Specific Antibody Positive Kidney Transplant Recipients", Transplant Direct, 2018;4(9):e379, 5 pages.

Jung, et al., "Cell-free DNA in the blood as a solid tumor biomarker—a critical appraisal of the literature", Clin Chim Acta., Nov. 11, 2010;411(21-22): doi: 10.1016/j.cca.2010.07.032. Epub Aug. 2, 2010., 1611-1624.

Jung, K. et al., "Cell-free DNA in the blood as a solid tulnor biomarker-A critical appraisal of the literature", Clinica Chimica Acta, vol. 411, 2010, 1611—1624.

Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.

Karapetis, et al., "K-ras mutations and benefit from cetuximab in advanced colorectal cancer", N Engl J Med., Oct. 23, 2008;359(17). doi: 10.1056/NEJM0a0804385., 1757-1765.

Keshavjee, S. H. et al., "The role of dextran 40 and potassium in extended hypothermic lung preservation for transplantation", The Journal of Thoracic and Cardiovascular Surgery, vol. 103, No. 2, 1992.

Khush, et al., "Circulating cell-free DNA as a non-invasive marker of pediatric heart transplant rejection and immunosuppressive treatment", J Heart Lung Transplantation, Apr. 2016. 35(4):Abstract 181, S75.

Khush, et al., "Noninvsive detection of graft injury after heart transplant using donor/\derived cell/\free DNA: A prospective multicenter study", Am J Transplant, Oct. 2019;19(10): doi: 10.1111/ajt.15339. Epub Apr. 8, 2019., 2889-2899.

Kindel, et al., "Early Changes in Donor Fraction Cell-free DNA in Newly Transplanted Heart Transplant Patients", ISHLT DF cfDNA declanation poster, 2018, 1 Page.

Kirkizlar, et al., "Detection of Clonal and Subclonal Copy-Number Variants in Cell-Free DNA from Patients with Breast Cancer Using a Massively Multiplexed PCR Methodology", Transl Oncol., Oct. 2015;8(5): doi: 10.1016/j.tranon.2015.08.004., 407-416.

Kuo, et al., "Preimplantation and prenatal genetic diagnosis of aromatic L-amino acid decarboxylase deficiency with and amplification refractory mutation system-quantitative polymerase chain reaction", Taiwan J Obstet Gynecol, Dec. 2011;50(4): doi: 10.1016/j.tjog.2011.10.012., 468-473.

Kustanovich, et al., "Life and death of circulating cell-free DNA", Cancer Biol Ther., 2019;20(8): doi: 10.1080/15384047.2019.1598759. Epub Apr. 16, 2019, 1057-1067.

Lajin, et al., "A quadruplex tetra-primer ARMS-PCR method for the simultaneous detection of TP53 Arg72Pro, IVS3 16bp Del/Ins and IVS6+62 A>G, and NQO1 C609T polymorphisms", Gene., Aug. 10, 2012; 504(2): Epub May 23, 2012., 268-273.

Lang, et al., "Optimized allele-specific real-time PCR assays for the detection of common mutations in KRAS and BRAF", J Mol Diagn., Jan. 2011;13(1): doi; 10.1016/j.jmoldx.2010.11.007. Epub Dec. 23, 2010., 23-28.

Laurent-Puig, et al., "Clinical relevance of KRAS-mutated subclones detected with picodroplet digital PCR in advanced colorectal cancer treated with anti-EGFR therapy", Clin Cancer Res., Mar. 1, 2015;21(5): doi: 10.1158/1078-0432.CCR-14-0983. Epub Sep. 23, 2014., 1087-1097.

Lecomte, et al., "Detection of free-circulating tumor-associated DNA in plasma of colorectal cancer patients and its association with prognosis", Int J Cancer, Aug. 10, 2002;100(5): doi: 10.1002/ijc.10526., 542-548.

Lee, et al., "Allele-Specific Quantitative PCR for Accurate, Rapid, and Cost-Effective Genotyping", Hum Gene Ther., Jun. 2016;27(6): doi: 10.1089/hum.2016.011. Epub Mar. 17, 2016., 425-435.

Lefebure, et al., "Prognostic value of circulating mutant DNA in unresectable metastic colorectal cancer", Ann Surg., Feb. 2010;251(2): doi: 10.1097/SLA.0b013e3181c35c87, 275-280.

Lehmann-Weman et al., Identification of Tissue-Specific Cell Death Using Methylation Patterns of Circulating DNA. Proc Natl Acad Sci US A. Mar. 29, 2016;113(13):E1826-34. doi: 10.1073/pnas.1519286113.E Epub Mar. 14, 2016.

Levy, et al., "Analysis of Cell-Free DNA to Assess Risk of Tumoremia Following Endoscopic Ultrasound Fine-Needle Aspiration of Pancreatic Adenocarcinomas", Clin Gastroenterol Hepatol., Oct. 2018;16(10): e1. doi: 10.1016/j.cgh.2018.02.048. Epub Mar. 8, 2018., 1632-1640.

Li, et al., "Multiplex co-amplification of 24 retinoblastoma gene exons after pre-amplification by long-distance PCR", Nucleic Acids Res., Feb. 1, 1996;24(3), 538-539.

Liang, et al. "Cationic nanoparticle as an inhibitor of cell-free DNA-induced inflammation", Nat Commun., Oct. 16, 2018;9(1):4291, doi: 10.1038/s41467-018-06603-5, 14 pages.

Lievre, et al., "KRAS mutations as an independent prognostic factor in patients with advanced colorectal cancer treated with cetuximab", J Clin Oncol., Jan. 20, 2008;26(3): doi: 10.1200/JCO.2007.12.5906., 374-379.

Liu, et al., "ABO chimerism determined by real-time polymerase chain reaction analysis after ABO-incompatible haematooietic stem cell transplantation", Blood Tranfus, Jan. 2013;11(1): doi: 10.2450/2012.0013-12. Epub Jul. 4, 2012., 43-52.

Liu, et al., "Comparison of next-generation sequencing systems", J Biomed Biotechnol., 2012;2012: doi: 10.1155/2012/251364. Epub Jul. 5, 2012., 1-11.

(56) References Cited

OTHER PUBLICATIONS

Lo, et al., "Plasma placental RNA alleclic ration permits noninvasive prenatal chromosomal aneuploidy detection", Nat Med., Feb. 2007;13(2): doi: 10.1038/nm1530. Epub Jan. 7, 2007., 218-223.
Lo, et al., "Transplantation monitoring by plasma DNA sequencing", Clin Chem., Jul. 2011;57(7): doi: 10.1373/clinchem.2011. 166686. PubMed PMID: 21566070., 941-942.
Luo, et al., "Detection of usual and atypical aldehyde dehydrogenase alleles by mismatch amplification mutation assay", Clin Chem Lab Med., Dec. 2001;39(12): doi 10.1515/CCLM.2001.189., 1195-1197.
Mak, et al., "Rapid diagnosis of Wilson disease by a 28-mutation panel: real-time amplification refractory mutation system in diagnosing acute Wilsonian liver failure", Clin Chim Acta., Dec. 2008; 398(1-2): doi: 10.1016/j.cca.2008.08.002. Epub Aug. 8, 2008., 39-42.
Manage, et al., "Genotyping single nucleotide polymorphisms in human genomic DNA with an automated and self-contained PCR cassette", J Mol Diagn., Sep. 2014;16(5): doi:10.1016/j.jmoldx. 2014.04.004. Epub Jul. 2, 2014., 550-557.
Martinez-Herrero, et al., "Cancer protection elicited by a single nucleotide polymorphism close to the adrenomedullin gene", J Clin Endocrinol Metab., Apr. 2013;98(4): doi 10.1210/jc.2012-4193. Epub Feb. 28, 2013., E807-E810.
Mehra, et al., "Gene expression profiles and B-type natriuretic peptide elevation in heart transplantatation: more than a hemodynamic marker", Circulation, Jul. 4, 2006;114(1 Suppl), I21-I26.
Mehra, et al., "International Society for Heart and Lung Transplanation working formulation of a standized nomenclature for cardiac allograft vasculopathy-2010", J Heart Lung Transplant, Jul. 2010;29(7) . doi: 10.1016/j.healun.2010.05.017., 717-727.
Mengel, et al., "The molecular phenotype of heart transplant biopsies: relationship to histopathological and clinical variable", Am J Transplant, Sep. 2010;10(9): doi: 10.1111/j.1600-6143.2010.03182. x., 2105-2115.
Misale, et al., "Emergence of KRAS mutations and acquired resistance to anti-EGFR therapy in colorectal cancer", Nature, Jun. 28, 2012;486(7404): doi: 10.1038/nature11156., 532-536.
Mouliere, et al., "Circulating Cell-Fee DNA from Colorectal Cancer Patients May Reveal High KRAS or BRAF Mutation Load", Transl Oncol., Jun. 1, 2013;6(3): doi 10.1593/tlo. 124445. Print Jun. 2013., 319-328.
Myers, et al., "ACR-PCR quantification of somatic oncomutation", Methods Mol Biol., 2014;1105: doi:10.1007/978-1-62703-739-6_27, 345-363.
Nakamura, N. et al. "Ex Vivo Liver Perfusion with Arterial Blood from a Pig with Ischemic Liver Failure" Artificial Organs 23(2): 153-160. (Year: 1999).
Newton, et al., "Analysis of any point mutation in DNA. The amplification refractory mutation system (ARM)", Nucleic Acids Res., Apr. 11, 1989;17(7): doi: 10.1093/nar/17.7.2503, 2503-2516.
North, et al., "Cell-free DNA donor fraction analysis in pediatric and adult heart transplant patients by multiplexed allele-specific quantitative PCR: Validation of a rapid and highly sensitive clinical test for stratification of rejection probability", PLoS One, Jan. 13, 2020;15(1):e0227385. doi: 10.1371/journal.pone.0227385. eCollection 2020., 48 pages.
Norton, S. E. et al., "A stabilizing reagent prevents cell-free DNA contamination by cellular DNA in plasma during blood sample storage and shipping as determined by digital PCR", Clin Biochem., vol. No. 15, Oct. 2013, 1561-1565.
Nui, A. et al "The Functional Integrity of a Normothermic Perfusion System Using Artifical Blood in Pig Liver" Journal of Surgical Research 131, 189-198 (Year: 2006).
Oeth, et al., "Qualitative and quantitative genotyping using single base primer extension coupled with matrix-assisted laser desorption/ionization time-of-flight mass spectrometry (MassARRAY®).", Methods Mol. Biol., 2009; 578, 307-343.
Olerup, O. et al., "HLA-DR typing by PCR amplification with sequence-specific primers (PCR-SSP) in 2 hours: an altenative to serological DR typing in clinical practice including donor-recipient matching in cadaveric transplantation", Tissue Antigens, vol. 39, No. 5, May 1992, 225-235.
Oros, et al., "Allele-specific competitive blocker PCR: a one-step method with applicability to pool screening", Hum Mutat., 1995:6(2): doi: 10.1002/humu.1380060209., 163-169.
Partpart-Li et al., The Effect of Preservative and Temperature on the Analysis of Circulating Tumor DNA. Clin Cancer Res. May 15, 2017;23(10):2471-2477. doi 10.1158/1078-0432.CCR—6-1691. Epub Nov. 8, 2016.
Parsons, et al., "Allele-specific competitive block-PCR detection of rare base substitution", Methods Mol Biol., 2005;291, 235-245.
PCT/US2017/059808, "International Preliminary Report on Patentability", dated May 16, 2019, 8 pages.
PCT/US2017/059808, "International Search Report and Written Opinion for Application", dated Jan. 25, 2018, 12 pages.
PCT/US2018/038598, "International Preliminary Report on Patentability", dated Jan. 2, 2020, 6 pages.
PCT/US2018/038598, "International Search Report and Written Opinion", dated Sep. 7, 2018, 8 pages.
PCT/US2018/038609, "International Preliminary Report on Patentability", dated Jan. 2, 2020, 7 pages.
PCT/US2019/038609, "International Search Report and Written Opinion", dated Sep. 10, 2018, 9 pages.
PCT/US2018/065845, "International Search Report and Written Opinion" dated Mar. 8, 2019, 7 pages.
PCT/US018/065845, "International Preliminary Report on Patentability" dated Jun. 25, 2020, 9 pages.
Peng, et al., "Comparison K-ras mutations in lung, colorectal and gastric cancer", Oncol Lett., Aug. 2014;8(2): doi: 10.3892/ol.2014. 2205. Epub May 30, 2014., 561-565.
Peyster, et al., "Advanced Morphologic Analysis for Diagnosing Allograft Rejection: The Case of Cardiac Transplant Rejection", Transplantation, Aug. 2018;102(8): doi 10.1097/TP0000000000002189., 1230-1239.
Price, et al., "Cost-effective interrogration of single nucleotide polymorphisms using the mismatch amplification mutation assay and capillary electrophoresis", Electrophoresis, Dec. 2010;31(23-24): doi: 10.1002/elps.201000379., 3881-3888.
Purhonen, et al., "Human plasma cell-free DNA as a predictor of infectious complications of neutropenic fever in hematological patients", Infect Dis (Lond)., Apr. 2015;47(4): doi: 10.3109/00365548. 2014.985711. Epub Feb. 9, 2015., 255-259.
Qin, et al., "Quantitative assessment of hematopoietic chimerism by quantitative real-time polymerase chain reaction of sequence polymorphism systems after hematopoietic stem cell transplantation", Chin Med J (Engl), Aug. 2011;124(15), 2301-2308.
Quail, et al., "A tale of three next generation sequencing platforms: comparison of Ion torrent, pacific biosciences and illumina MiSeq sequencers", BMC Genomics, Jul. 24, 2012;13:341. doi: 10.1185/1471-2164-13-641, 13 pages.
Raemdonck, Dirk Van et al., "Ex-vivo lung perfusion", Transplant International, vol. 28, Issue 6, Special Issue; Focus Issue: Machine Perfusion, 2014, 643-656.
Ragalie, et al., "Description of Longitudinal Measurement of Donor Fraction of Cell-Free DNA and Correlation to Clinical Outcomes", ISHLT poster, 2018, 1 page.
Ragalie, et al., "Noninvasive Assay for Donor Fraction of Cell-Free DNA in Pediatric Heart Transplant Recipients", J Am Coll Cardiol., Jun. 26, 2018;71(25): doi: 10.1016/j.jacc.2018.04.026, 2982-2983.
Richmond, et al., "Donor fraction cell-free DNA and rejection in adult and pediatric heart transplantation", J Heart Lung Transplant, May 2020;39(5): doi: 10.1016/j.healun.2019.11.015. Epub Nov. 29, 2019., 454-463.
Roedder, et al., "Biomarkers in solid organ transplantation: establishing personalized transplantation medicine", Genome Med., Jun. 8, 2011;3(6):37, 12 pages.
Sairafi et al., Donor Cell Composition and Reactivity Predict Risk of Acute Graft-versus-Host Disease After Allogeneic Hematopoietic Stem Cell Transplantation. J Immunol Res. 2016; 2016;5601204. doi: 10.1155/2016/5601204. Epub Nov. 14, 2016.
Sanmamed, et al., "Quantitative cell-free circulating BRAFV600E mutation analysis by use of droplet digital PCR in the follow-up of

(56) References Cited

OTHER PUBLICATIONS patients with melanoma being treated with BRAF inhibitors", Clin Chem., Jan. 2015;61(1): doi: 10.1373/clinchem.2014.230235. Epub Nov. 19, 2014., 297-304.

Sapio, et al., "Detection of BRAF mutation in thyroid papillary carcinomas by mutant allele-specific PCR amplification (MASA)", Eur J Endocrinol., Feb. 2006;154(2): doi: 10.153/eje.1.02072, 341-348.

Saukkonen, et al., "Cell-free plasma DNA as a predictor of outcome in severe sepsis and septic shock.", Clin Chem., Jun. 2008;54(6): doi: 10.1373/clinchem.2007.101030. Epub Apr. 17, 2008. PubMed PMID: 18420731., 1000-1007.

Schnittger, et al., "Development and validation of a real-time quantification assay to detect and monitor BRAFV600E mutations in hairy cell leukemia", Blood., Mar. 29, 2012;119(13): doi: 10.1182/blood-2011-10-383323. Epub Feb. 13, 2012., 3151-3154.

Schutz, et al., "Graft-derived cell-free DNA, a noninvasive early rejection and graft damage marker in liver transplantation: A prospective, observational, multicenter cohort study", PLoS Med., Apr. 25, 2017;14(4):e1002286. doi 10.1371/journal.pmed.1002286. eCollection Apr. 2017., 19 pages.

Schutz, E. et al., "Graft-drived cell-free DNA, a noninvasive early rejection and graft damage marker in liver transplantation: A prospective, observational, multicenter cohort study", PLOS Medicine, vol. 14, No. 4, Apr. 25, 2017, 19 pgs.

Schwarzenbach, et al., "Cell-free nucleic acids as biomarkers in cancer patients", Nat Rev Cancer, Jun. 2011;11(6): doi: 10.1038/nrc3066. Epub May 12, 2011, 426-437.

Scott, et al. "Elevated nuclear and mitochondrial cell-free deoxyribonucleic acid measurements are associated with death after infant cardiac surgery", J Thorac Cardiovas Surg., Aug. 2022;164(2): doi: 10.1016/j.jtcvs.2021.10.066. Epub Dec. 24, 2021., 367-375.

Scott, et al., "Total Cell-Free DNA Predicts Death and Infection Following Pediatric and Adult Heart Transplantation", Ann Thorac Surg., Oct. 2021;112(4): doi: 10.1016/j.athoracsur.2020.08.006. Epub Oct. 8, 2020., 1282-1289.

Sefrioui, et al., "Clinical value of chip-based digital-PCR platform for the detection of circulating DNA in metastatic colorectal cancer", Dig Liver Dis., Oct. 2015;47(10): doi: 10.1016/j.dld.2015.05.023. Epub Jun. 5, 2015, 884-890.

Selzner, Markus et al., "Normothermic Ex Vivio Liver Perfusion Using Steen Solution as Perfusate for Human Liver Transplantation: First North American Results", Liver Transplantation, vol. 22, Issue 11, 2016.

Sheffield, et al., "Attachment of a 40-base-pair G + C-rich sequence (GC-clamp) to genomic DNA fragments by the polymerase chain reaction results in improved detection of single-base changes", Proc Natl Acad Sci U S A, Jan. 1989;86(1), 232-236.

Shi, et al., "Development of a single multiplex amplification refractory mutation system PCR for the detection of rifampin-resistant Mycobacterium tuberculosis", Gene., Nov. 1, 2013; 530(1): Epub Aug. 19, 2013, 95-99.

Shimabukuro-Vornhagen, et al., "Cytokine release syndrom", J Immunother Cancer, Jun. 15, 2018;6(1):56. doi. 10.1186/s40425-018-0343-9, 14 pages.

Sigdel, et al., "A rapid noninvasive assay for the detection of renal transplant injury", Transplantation, Jul. 15, 2013;96(1); doi: 10.1097/TP.0b013e318295ee5a., 97-101.

Singh, et al., "Aspergillus infections in transplant recipients", Clin Microbiol Rev., Jan. 2005;18(1), 44-69.

Snyder et al., Cell-free DNA Comprises an In Vivo Nucleosome Footprint That Informs Its Tissues-Of-Origin. Cell. Jan. 14, 2016;164(1-2):57-68. doi: 1.1016/j.cell.2015.11.050.

Snyder, et al., "Universal noninvasive detection of solid organ transplant rejection", Proc Natl Acad Sci U S A, Apr. 12, 2011;108(15); doi: 10.1073/pnas.1013924108. Epub Mar. 28, 2011. PubMed PMID: 21444804: PubMed Central PMCID: PMC3076856., 6229-6234.

Sparks, et al., "Noninvasive prenatal detection and selective analysis of cell-free DNA obtained from maternal blood: evaluation for trisomy 21 and trisomy 18", Am J Obstet Gynecol., Apr. 2012;206(4): doi: 10.1016/j.ajog.2012.01.030. Epub Jan 26, 2012.e1-319.e9.

Sparks, et al., "Selective analysis of cell-free DNA in maternal blood for evaluation of fetal trisomy", Prenat Diagn., Jan. 2012;32(1). Epub Jan. 6, 2012., 3-9.

Spindler, et al., "Cell-free DNA in healthy individuals, noncancerous disease and strong prognostic value in colorectal cancer", Int J Cancer, Dec. 15, 2014;135(12): doi: 10.1002/ijc.28946. Epub Jun. 17, 2014, 2984-2991.

Spindler, et al., "KRAS-mutated plasma DNA as predictor of outcome from irinotecan monotherapy in metastatic colorectal cancer", Br J Cancer, Dec. 10, 2013;109(12). doi. 10.1038/bjc2013.633. Epub Nov. 21, 2013., 3067-3072.

Spindler, et al., "Quantitative cell-free DNA, KRAS, and BRAF mutations in plasma from patients with metastatic colorectal cancer during treatment with cetuximab and irinotecan", Clin Cancer Res., Feb. 15, 2012;18(4). doi: 10.1158/1078-0432.CCR-11-0564. Epub Jan. 6, 2012., 1177-1185.

Spindler, K.L. G. et al., "Cell-free DNA in healthy individuals, noncancerous disease and strong prognostic value in colorectal cancer", International Journal of Cancer, vol. 135, 2014, 2984-2991.

Stein, "Next-Generation Sequencing Update", Genetic Engineering & Biotechnology News, Sep. 1, 2008; 28(15). https://www.genengnews.com/magazine/97/next-generation-sequencing-update/, 10 pages.

Steinborn, et al., "Coexistence of Bos taurus and B. indicus mitochondrial DNAs in nuclear transfer-drived somatic cattle clones", Genetics Oct. 2002;162(2), 823-829.

Stemmer, et al., "Use of magnetic beads for plasma cell-free DNA extraction: toward automation of plasma DNA analysis for molecular diagnostics", Clin Chem., Nov. 2003;49(11): PubMed PMID: 14578335., 1953-1955.

Stone, J. P. et al., "Altered Immunogenicity of Donor Lungs via Removal of Passenger Leukocytes Using Ex Vivo Lung Perfusion", American Journal of Transplantation, vol. 16, 2016, 33-43.

Stone, J. P. et al., "Ex Vivo Normothermic Perfusion Induces Donor-Derived Leukocyte Mobilization and Removal Prior to Renal Transplantation", Kidney In Rep., vol. 1, No. 4, Aug. 6, 2016, 230-239.

Strausberg, et al., "*Homo sapiens* placenta-specific 4, mRNA (cDNA clone MGC;120720 Image:7939530), complete cds", GenBank Submission; Accession No. BC093685, version BC093685.1., Jan. 18, 2007, 2 Pages.

Strohmeier, et al., "Multiplex genotyping of KRAS point mutations in tumor cell DNA by allele-specific real-time PCR on a centrifugal microfluidic disk segment", Microchimica Acta., 2014;181 (13-14), 1681-1688.

Suzuki, et al., "Characterization of circulating DNA in healthy human plasma", Clin Chim Acta., Jan. 2008;387(1-2):doi; 10.1016/j.cca.2007.09.001. Epub Sep. 8, 2007., 55-58.

Swinkels, et al., "Effects of blood-processing protocols on cell-free DNA quantification in plasma", Clin Chem., Mar. 2003;49(3): PubMed PMID: 12600978, 525-526.

Tabernero, et al., "Analysis of circulating DNA and protein biomarkers to predict the clinical activity of regorafenib and assess prognosis in patients with metastatic colorectal cancer: a retrospective, exploratory analysis of the Correct trial", Lancet Oncol., Aug. 2015;16(8): doi: 10.1016/S1470-2045(15)00138-2. Epub Jul. 13, 2015., 937-948.

Taira, et al., "Novel high-speed droplet-allele specific-polymerase chain reaction: application in rapid genotyping of single nucleotide polymorphisms", Clin Chim Acta., Sep. 23, 2013;424: doi: 10.1016/j.cca.2013.04.024. Epub May 17, 2013., 39-46.

Taira, et al., "Quantitative monitoring of single nucleotide mutations by allele-specific quantitative PCR can be used for the assessment of minimal residual disease in patients with hematological malignancies throughout their clinical course", Clin Chim Acta., Jan. 14, 2011;412(1-2): doi:10.1016/j.cca.2010.09.011. Epub Sep. 16, 2010., 53-58.

Takai, et al., "Clinical utility of circulating tumor DNA for molecular assessment in pancreatic cancer", Sci Rep., Dec. 16, 2015;5:18425. doi: 10.1038/srep18425., 10 pages.

Taly, et al., "Multiplex picodroplet digital PCR to detect KRAS mutations in circulating DNA from the plasma of colorectal cancer

(56) References Cited

OTHER PUBLICATIONS patients", Clin Chem., Dec. 2013;59(12): doi: 10.1373/clinchem. 2013.206359. Epub Aug. 12, 2013., 1722-1731.

Tamkovich, et al., "Circulating nucleic acids in blood of healthy male and female donors", Clin Chem., Jul. 2005;51(7): PubMed PMID: 15976134., 1317-1319.

Tanem, et al., "Abstract 16873: Association of Preoperative Cell-Free DNA Levels and Outcome Following Pediatric Cardiopulmonary Bypass", Circulation, Nov. 17, 2020; 142(S3): https://doi.org/10.1161/circ.142.suppl_3.16873., 1-6.

Thierry, et al., "A Targeted Q-PCR-Based Method for Point Mutation Testing by Analyzing Circulating DNA for Cancer Management Care", Methods Mol Biol., 2016;1392: doi: 10.1007/978-1-4939-3360-0_1, 1-16.

Thierry, et al., "Clinical validation of the detection of KRAS and BRAF mutations from circulating tumor DNA", Nat Med., Apr. 2014;20(4): doi: 10.1038/nm.3511, Epub Mar. 23, 2014., 430-435.

Tomita-Mitchell, et al., "Human gene copy number spectra analysis in congenital heart malformations", Physiol Genomics, May 1, 2012;44(9): doi: 10.1152/physiolgenomics.00013.2012. Epub Feb. 7, 2012., 518-541

Tong, et al., "Diagnostic developments involving cell-free (circulating) nucleic acids", Clin Chim Acta., Jan. 2006;363(1-2): Epub Aug. 26, 2005. Review. PubMed PMID: 16126188, 187-196.

Umetani, N. et al., "Increased Integrity of Free Circulating DNA in Sera of Patients with colorectal or Periampullary Cancer: Direct Quantitative PCR for ALU Repeats", Clinical Chemisty, vol. 52, No. 6, 2006, 1062-1069.

Valenza, F. et al., "The Consumption of Gluconse During Ex Vivo Lung Perfusion Correlates with Lung Edema", Transplantation Proceedings, vol. 43, 2011, 993-996.

Van Orsouw, et al., "Rapid design of denaturing gradient-based two-dimensional electrophoretic gene mutational scanning test", Nucleic Acids Res., May 15, 1998;26(10), 2398-2406.

Van Raemdonck et al., "Ex-vivo lung perfusion" Transplant International, vol. 28, Issue 6, Special Issue: Focus Issue: Machine Perfusion, Jun. 2015, pp. 643-656 (First published: Mar. 15, 2014) (Year: 2014).

Vannucchi, et al., "A quantitative assay for JAK2(V617F) mutation in myeloproliferative disorders by ARMS-PCR and capillary electrophoresis", Leukemia, Jun. 2006;20(6), 1055-1060.

Verhoeven et al., Biomarkers to Assess Graft Quality During Conventional and Machine Preservation in Liver Transplantation. J Hepatol. Sep. 2014;61(3):672-84. doi: 10.1016/j.jhep.2014.04.031. Epub May 4, 2014.

Veseloskva, "The use of cell-free nucleic acids in maternal plasma for non-invasive prenatal diagnosis and mongenic diseases, placental insufficiency-related complications and Down syndrome", Thesis from Charles University in Prague, 2011, 104 pages.

Vlaminck, I. D. et al., "Circulating Cell-Free DNA Enables Noninvasive Diagnosis of Heart Transplant Rejection", Sci Transl Med., vol. 6, No. 241, Jun. 18, 2014, 26 pages.

Wangkumhang, et al., "WASP: a Web-based Allele-Specific PCR assay desigining tool for detecting SNPs and mutations", BMC Genomics, Aug. 14, 2007;8:275, 9 Pages.

Wangkumhang, P. et al., "WASP: a Web-based Allele-Specific PCR assay designing tool for detecting SNPs and mutations", BMC Genomics, vol. 8, No. 275, Aug. 14, 2007, 9 pgs.

Wapner, et al., "Expanding the scope of noninvasive prenatal testing: detection of fetal micodeletion syndromes", Am J Obstet Gynecol., Mar. 2015;212(3): doi: 10.1016/j.ajog.2014.11.041. Epub Dec. 2, 2014., 332.e1-332.e9.

Wilkins, et al., "IMP PCR primers detect single nucleotide polymorphisms for Anopheles gambiae species identification, Mopti and Savanna rDNA types, and resistance to dieldrin in Anopheles arabiensis", Malar J., Dec. 19, 2006;5:125., 7 pages.

Woude, et al., "Methods of identifying drugs with selective effects against cancer cells", Oct. 7, 1997, Nucleic acid sequence search reports AC: 151794, Accession I51796., 2 Pages.

Yamada, et al., "Detection of K-ras gene mutations in plasma DNA of patients with pancreatic adenocarcinoma: correlation with clinicopathological features", Clin Cancer Res., Jun. 1998;4(6), 1527-1532.

Yi, et al., "PCR/LDR/capillary electrophoresis for detection of single-nucleotide differences between fetal and maternal DNA in maternal plasm", Prenat Diagn., Mar. 2009;29(3): doi: 1.1002/pd. 2072., 217-222.

Zangwill, et al., "Effect of endomyocardial biopsy on levels of donor-specific cell-free DNA", J Heart Lung Transplant, Oct. 2019;38(10):doi: 10.1016/j.healun.2019.06.005. Epub Jun. 28, 2019., 1118-1120.

Zhang, et al., "A nove multiplex tetra-primer ARMS-PCR for the simultaneous genotyping of six single nucleotide polymorphisms associated with female cancers", PLoS One, Apr. 17, 2013;8(4):e62126. doi: 10.1371/journal.pone.0062126. Print 2013., 8 pages.

\* cited by examiner

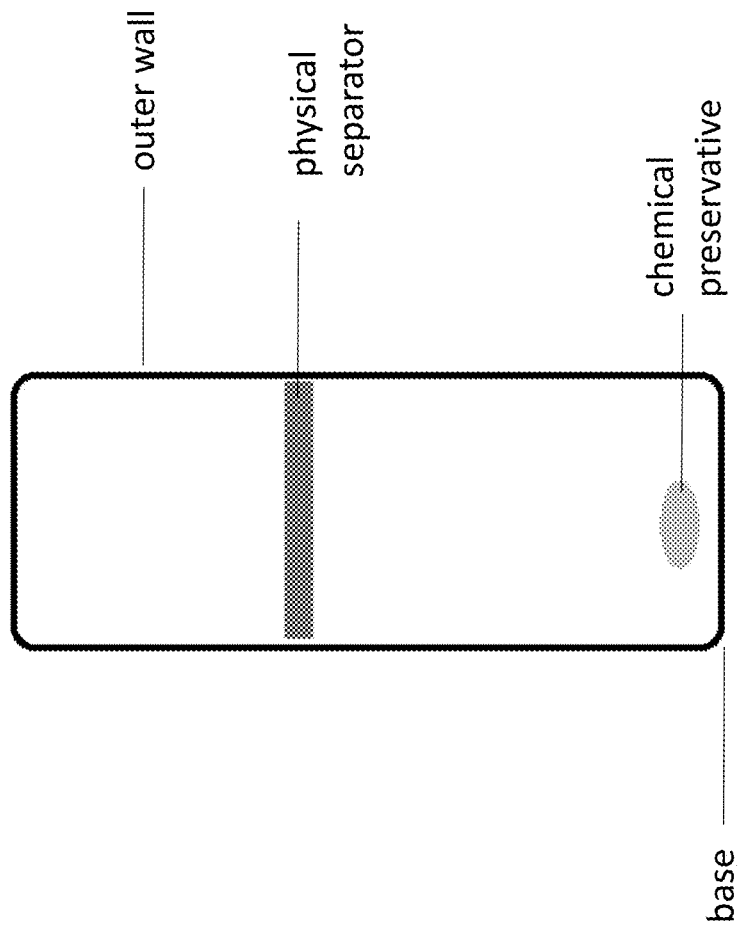

MATERIALS AND METHODS FOR PROCESSING BLOOD SAMPLES

CROSS-REFERENCE TO RELATED APPLICATION

This application claims priority to U.S. Provisional Application No. 62/829,320, filed Apr. 4, 2019, which is incorporated herein by reference in its entirety.

FIELD OF INVENTION

Provided herein is technology relating to cell-free DNA. In particular, the technology relates to methods and materials for the preparation and handling of blood samples for future use in applications involving cell-free DNA.

BACKGROUND

Cell-free DNA (cf-DNA) can be isolated from biological samples such as whole blood, plasma, serum, other body fluids (e.g., organ perfusate fluids) and can be analyzed for a variety of purposes, such as transplant monitoring including general assessments of in vivo tissue damage. However, cellular lysis, such as from white blood cells (WBCs) can occur during or after sample collection or processing and result in genomic DNA being released from those cells. This can result in additional DNA from the subject (self) being introduced and can result in the dilution of non-self, such as a transplant donor, fraction. Therefore, what is needed are methods of preparing and handling samples comprising cf-DNA that reduce the risk of cell lysis from WBCs.

SUMMARY

Provided herein are materials and methods for the preparation and handling of blood samples. In some embodiments, disclosed herein are tubes for collecting a blood sample, the tube comprising: an outer wall and a base defining an internal volume for containing the blood sample; a chemical preservative disposed in the internal volume; and a physical separator disposed in the internal volume. Further provided herein are methods for processing a blood sample. The methods comprise providing a first container comprising a blood sample; centrifuging the first container at a first fixed speed to separate the blood sample into at least a plasma component and a blood cell component; isolating the plasma component; and centrifuging the isolated plasma component at a second fixed speed.

Additional embodiments will be apparent to persons skilled in the relevant art based on the teachings contained herein.

BRIEF DESCRIPTION OF THE DRAWINGS

FIG. 1 shows a tube as described herein comprising a base, an outer wall, a chemical preservative, and a physical separator.

DETAILED DESCRIPTION

Described herein are materials and methods for collection and processing of blood samples. In particular embodiments, provided herein are tubes for collection of blood samples. In other embodiments, provided herein are methods for processing blood samples. The materials and methods provided herein may be useful for collection and processing of blood samples suitable for downstream applications involving cell-free DNA.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the term "sample" and "specimen" are used interchangeably, and in the broadest senses. In one sense, sample is meant to include a blood sample. The blood sample may be a whole blood sample. The terms "whole blood" or "whole blood sample" as used interchangeably herein refer to a blood sample wherein none of the components (e.g. plasma, white blood cells, red bloods cells, or platelets) have been removed. In some instances, the blood sample comprises at least a "plasma component" and a "blood cell component." The term "plasma component" refers to the portion of the blood sample that is devoid of any cells. The term "blood cell component" refers to the portion of the blood sample that contains blood cells. The term "blood cells" as used herein refers to any type of blood cell, including red blood cells, white blood cells, and platelets. The blood sample may be obtained or isolated from any suitable subject.

As used herein, the terms "subject" and "patient" refer to any animal, such as a dog, cat, bird, livestock, and particularly a mammal, preferably a human.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

Embodiments of the Technology

Although the disclosure herein refers to certain illustrated embodiments, it is to be understood that these embodiments are presented by way of example and not by way of limitation.

1. Tubes

In some embodiments, provided herein are tubes for collecting a blood sample. The tubes comprise an outer wall and a base defining an internal volume for containing the blood sample, a chemical preservative disposed in the internal volume, and a physical separator disposed in the internal volume. The outer wall and/or base of the tube may be any suitable material. For example, the outer wall and/or base of the tube may comprise glass. As another example, the outer wall and/or base of the tube may comprise plastic. In some embodiments, the outer wall and base of the tube comprise a suitable plastic material.

The tubes may be any suitable size for collection of the desired volume of blood. For example, the tube may be a suitable size for the collection of about 1 ml to about 20 ml of blood. For example, the tube may be a suitable size for the collection of about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, or about 20 ml of blood.

a. Chemical Preservative

The tubes comprise a chemical preservative disposed in the internal volume of the tube. The chemical preservative may be any suitable preservative to stabilize blood cells, such as white blood cells. Stabilization of blood cells comprises reducing the risk of cell lysis in the blood sample. Accordingly, stabilization of blood cells comprises reducing the risk of release of genomic DNA from the blood cells into the sample.

In some embodiments, the chemical preservative may be any one or more of diazolidinyl urea, aldehyde derivatives (e.g. paraformaldehyde, formaldehyde, metaformaldehyde), poloxamers (e.g. P118, P331), polyethylene glycol (PEG) (e.g. PEG 8000), DMSO, glycerol, sucrose, propranolol, dex-propranolol, bilayer lipid membrane stabilizers (e.g. methyacrylate monomers, methyacrylate polymers, bis-Elienoyl phosphatidylcholine), TransFix®, and Cytochex®. For example, methyacrylate monomers include ethylene glycol dimethacrylate and butyl methacrylate.

b. Physical Separator

The tubes further comprise a physical separator disposed in the internal volume of the tube. The physical separator substantially separates the blood sample into at least a plasma component and a blood cell component. For example, the physical separator may substantially separate the blood sample into at least a plasma component and a blood cell component when the tube is centrifuged. The physical separator may be designed to migrate in the tube during centrifugation such that the physical separator substantially separates the blood sample into at least a plasma component and a blood cell component after the tube has been centrifuged. Separation of the blood sample into at least a plasma component and a blood cell component may be achieved by centrifuging the tube at any suitable speed. For example, the tube may be centrifuged at a speed ranging from about 500×g to about 2000×g. For example, the tube may be centrifuged at about 500×g, about 600×g, about 700×g, about 800×g, about 900×g, about 1000×g, about 1100×g, about 1200×g, about 1300×g, about 1400×g, about 1500×g, about 1600×g, about 1700×g, about 1800×g, about 1900×g, or about 2000×g.

The blood cell component may comprise a red blood cell component and a white blood cell component. Accordingly, the physical separator may substantially separate the blood sample into a plasma component, a white blood cell component, and a red blood cell component. The white blood cell component may include both white blood cells and platelets. A white blood cell component including both white blood cells and platelets is also referred to herein as a "buffy coat".

The physical separator may additionally prevent aspiration of the blood cell component during subsequent isolation of the plasma component from the tube. For example, the physical separator may prevent aspiration of cells in the buffy coat (e.g., white blood cells and/or platelets) during subsequent isolation of the plasma component from the tube.

The physical separator may be any suitable material. For example, the physical separator may be a gel, such as a polyester-based polymer gel. The physical separator may also be referred to herein as a "plug" or a "gel plug".

The tubes described herein may be used in a method for collecting a blood sample, comprising adding the blood sample to a tube as described herein.

2. Sample Processing

In some embodiments, provided herein are methods for processing a blood sample. The methods comprise providing a first container comprising a blood sample. For example, the first container may comprise a whole blood sample. Providing a first container comprising a blood sample may include isolating blood from a subject into the first container (e.g., drawing blood from the subject) or may include obtaining a first container that already contains the blood sample. In some embodiments, the methods for processing a blood sample are performed less than 7 hours after blood has been obtained from the subject. For example, the methods for processing a blood sample may be performed less than 7 hours, less than 6 hours, less than 5 hours, less than 4 hours, less than 3 hours, less than 2 hours, or less than 1 hour after blood has been obtained from the subject.

The methods further comprise centrifuging the first container at a first fixed speed to separate the blood sample into at least a plasma component and a blood cell component. For example, centrifuging the first container at the first fixed speed may separate the blood sample into a plasma component, a white blood cell component, and a red blood cell component. The white blood cell component may include both white blood cells and platelets.

The first fixed speed may be any suitable speed for separation of the blood sample. For example, the first fixed speed may be any speed ranging from about 500×g to about 2000×g. For example, the first fixed speed may be about 500×g, about 600×g, about 700×g, about 800×g, about 900×g, about 1000×g, about 1100×g, about 1200×g, about 1300×g, about 1400×g, about 1500×g, about 1600×g, about 1700×g, about 1800×g, about 1900×g, or about 2000×g.

Centrifugation at the first fixed speed may be performed for any suitable duration of time. For example, centrifugation at the first fixed speed may be performed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. In some embodiments, centrifugation at the first fixed speed is performed for 10 minutes.

In some embodiments, the white blood cell component may be isolated after centrifuging the first container at the first fixed speed. The isolated white blood cell component may be stored at a suitable temperature. For example, the isolated white blood cell component may be stored at a temperature of −20'C or colder. For example, the isolated white blood cell component may be stored at a temperature of about −20° C., about −30° C., about −40° C., about −50° C., about −60° C., about −70° C., or about −80° C.

The methods further comprise isolating the plasma component and centrifuging the isolated plasma component at a second fixed speed. After centrifuging at the second fixed speed, the resulting, further purified plasma component is isolated. In some embodiments, this plasma component is isolated and store at a suitable temperature. For example, the isolated plasma component may be stored at a temperature of −20° C. or colder. For example, the isolated plasma component may be stored at a temperature of about −20° C., about −30° C., about −40° C., about −50° C., about −60° C., about −70° C., or about −30° C.

The second fixed speed may be any suitable speed. For example, the second fixed speed may be any speed ranging from about 500×g to about 2000×g. For example, the first fixed speed may be about 500×g, about 600×g, about 700×g, about 800×g, about 900×g, about 1000×g, about 1100×g, about 1200×g, about 1300×g, about 1400×g, about 1500×g, about 1600×g, about 1700×g, about 1800×g, about 1900×g, or about 2000×g.

Centrifugation at the second fixed speed may be performed for any suitable duration of time. For example, centrifugation at the second fixed speed may be performed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. In some embodiments, centrifugation at the second fixed speed is performed for 10 minutes.

In some embodiments, the first fixed speed and the second fixed speed are different. In other embodiments, the first fixed speed and the second fixed speed may be the same. For example, the first fixed speed and the second fixed speed may each be 1100×g. In other embodiments, the first fixed speed and the second fixed speed may each be 1400×g.

The first container may comprise any suitable tube. In some embodiments, the first container may comprise a tube having an outer wall and a base defining an internal volume for containing the blood sample, a chemical preservative disposed in the internal volume, and a physical separator disposed in the internal volume as described herein. However, the methods for processing a blood sample described herein may also be performed with other suitable first containers. For example, the first container may be a tube comprising a chemical preservative disposed in the internal volume of the tube but lacking a physical separator disposed in the internal volume. Alternatively, the first container may be a tube comprising a physical separator disposed in the internal volume of the tube but lacking a chemical preservative designed to stabilize white blood cells.

3. Applications

The tubes and sample processing methods described herein may be used in a variety of downstream applications. For example, the plasma isolated after the second centrifugation may be used for detection and/or quantification of cell-free DNA. Cell-free DNA from plasma collected in the disclosed tubes or by the described methods can be used for a variety of applications. Suitable applications for cell-free DNA include rare variant analysis such as in non-invasive prenatal testing, liquid biopsy for cancer, and transplant monitoring. Exemplary methods for methods involving analysis of cell-free DNA are provided in U.S. Pat. Nos. 10,385,396, 10,472,680, U.S. Patent Publication No. 20200032340 A1, U.S. Patent Publication No. 20190367972 A1, PCT Publication No. WO2018237075 A1, PCT Publication No. WO2018237081 A1, PCT Publication No. WO2018237078 A1, PCT Publication No. WO2019035995 A1, and PCT Publication No. WO2019118926 A1, each of which are incorporated herein by reference in their entireties.

Cell-free DNA may also be determined by a MOMA assay. Any one of the tubes or methods provided herein can be used in a MOMA assay such as described in PCT Publication No. WO2016176662 A1, PCT Publication No. WO2019217918A1, PCT Publication No. WO2017190104A1, PCT Publication No. WO2017190105A1, PCT Publication No. WO2017190106A1, and PCT Publication No. WO2018085597A1, each of which are incorporated herein by reference in their entireties.

Downstream use of the samples (e.g. the isolated plasma component and/or the isolated white blood cell component) obtained by the methods described herein may occur at the same site that the blood sample was processed (e.g. subjected to the first and second centrifugation steps) or at a different site. Additionally, the blood sample may be isolated from the subject at the same site that the blood sample is processed or at a different site.

For example, the blood sample may isolated from the subject at a first site, such as a hospital or a clinic. The isolated blood may be placed in a suitable container and processed by the methods described herein at the first site. In some embodiments, the isolated blood may be placed in a tube comprising a chemical preservative and a physical separator as described herein. The isolated blood components (i.e. the isolated plasma component and/or isolated white blood cell component) obtained from the sample by the processing methods described herein may be used at the first site for the desired downstream application. Alternatively, the isolated blood components obtained by the processing method may be transported to a second site for downstream use.

If the isolated blood components are to be transported to a second site for downstream use, proper storage and handling of the isolated blood components before and during transportation may prevent unwanted damage prior to downstream use. In some embodiments, the isolated blood components may be stored at the first site at a temperature of −20° C. or colder until the isolated blood components are frozen. For example, the isolated plasma component and/or isolated white blood cell component may be stored at a temperature of about −20° C. to about −80° C. for at least one hour (e.g. at least 1 hour, at least 2 hours, at least 3 hours, at least 4 hours, at least 5 hours, at least 6 hours, at least 7 hours, at least 8 hours, at least 9 hours, at least 10 hours, at least 11 hours, or at least 12 hours). The frozen isolated blood components may then be packaged and shipped to the desired second site. Suitable packaging materials include absorbent pouches, biohazard bags, cold-packs, ice, dry-ice, boxes (e.g. Styrofoam boxes), and the like. For example, the frozen isolated blood components may packaged in a box, such as a Styrofoam box, containing dry-ice such that the samples remain frozen during shipment to the second site. The temperature of the shipping environment may also be monitored. For example, a temperature logger may be placed on box containing the samples (e.g., on a lid of the box) or in the box containing the samples.

4. Kits

It is contemplated that embodiments of the technology are provided in the form of a kit. The kits comprise embodiments of the materials and methods described herein, and instructions for use of the kit. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. For example, the kits may comprise one or more tubes for collecting a blood sample as described herein. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

EXAMPLES

Example 1

During the development of embodiments of the technology provided herein, it was demonstrated that tubes comprising a physical separator and a chemical preservative demonstrates reduced cell lysis in plasma compared to tubes comprising only a chemical preservative or only a physical separator.

Blood was drawn from four different individuals into 3 different tube types (one with chemical preservative, one without chemical preservative, and one with a physical cell separator). Cell lysis in plasma was lower from tubes that used a cell preservation in comparison with tubes without a cell preservation chemical.

Levels of cell lysis in a cell tube with a chemical preservative a tube with a separator plug, and a tube comprising both a chemical preservative and a physical separator were compared. The combination tube had the least cell lysis.

In a follow-up experiment, the tubes were tested again with samples from 5 different donors. Cell lysis was lowest in the combination tube.

Taken together, these results demonstrate that the combination tube was superior to tubes without preservatives or separation or tubes having only preservatives or separation. The combination tubes offer superior cell-free DNA tubes for analysis for non-invasive applications such as cancer, transplant rejection, and prenatal testing, among other uses.

I claim:

1. A method for processing a blood sample, the method comprising:
   a. providing a tube comprising
      an outer wall and a base defining an internal volume for containing the blood sample;
      a chemical preservative disposed in the internal volume, wherein the chemical preservative comprises one or more of metaformaldehyde, paraformaldehyde, poloxamer, glycerol, propranolol, dex-propranolol, methacrylate monomer, methacrylate polymer, or bis-dienoyl phosphatidylcholine;
      a physical separator disposed in the internal volume, wherein the physical separator substantially separates the blood sample into at least a plasma component and a blood cell component when the tube is centrifuged and prevents aspiration of the blood cell component during subsequent isolation of the plasma component from the tube; and
      a blood sample disposed in the tube;
   b. centrifuging the tube at a first fixed speed to separate the blood sample into at least a plasma component and a blood cell component;
   c. isolating the plasma component; and
   d. centrifuging the isolated plasma component at a second fixed speed to obtain further purified plasma component, wherein the first fixed speed and the second fixed speed are each independently selected from a speed ranging from 500×g to 2000×g.

2. The method of claim 1, further comprising isolating the further purified plasma component after step d.

3. The method of claim 2, further comprising storing the isolated further purified plasma component at a temperature of −20° C. or colder.

4. The method of claim 1, wherein the blood cell component includes a white blood cell component and a red blood cell component.

5. The method of claim 4, further comprising isolating the white blood cell component after step b.

6. The method of claim 5, wherein the method further comprises storing the isolated white blood cell component at a temperature of −20° C. or colder.

7. The method of claim 1, wherein the first fixed speed and the second fixed speed are the same.

8. The method of claim 7, wherein the first fixed speed and the second fixed speed are each 1100×g.

9. The method of claim 7, wherein the first fixed speed and the second fixed speed are each 1400×g.

10. The method of claim 2, further comprising determining an amount of cf-DNA in the further purified isolated plasma component.

* * * * *